United States Patent [19]

Zdybak

[11] 4,427,449

[45] Jan. 24, 1984

[54] ANIONIC BITUMINOUS EMULSIONS

[75] Inventor: Walter T. Zdybak, Bellingham, Wash.

[73] Assignee: Georgia-Pacific Corporation, Atlanta, Ga.

[21] Appl. No.: 387,512

[22] Filed: Jun. 11, 1982

[51] Int. Cl.$^3$ .......................... C08L 95/00; C09D 3/24
[52] U.S. Cl. .................................. 106/277; 252/311.5
[58] Field of Search ...................... 106/277; 252/311.5

[56] References Cited

U.S. PATENT DOCUMENTS

| | | | |
|---|---|---|---|
| 2,332,542 | 10/1943 | Watts et al. | 252/311.5 |
| 2,494,708 | 1/1950 | Jesseph | 252/311.5 |
| 2,782,169 | 2/1957 | Brown | 252/311.5 |
| 2,978,342 | 4/1961 | Lefebvre | 106/123 |
| 3,123,569 | 3/1964 | Borgfeldt | 252/311.5 |
| 3,126,350 | 3/1964 | Borgfeldt | 252/311.5 |
| 3,578,651 | 5/1971 | Ludwig | 260/124 |
| 3,718,639 | 2/1973 | Falkehag | 260/124 A |
| 3,956,002 | 5/1976 | Moorer | 106/277 |
| 4,017,419 | 4/1977 | Ludwig et al. | 252/311.5 |
| 4,088,505 | 5/1978 | Moorer | 106/277 |

FOREIGN PATENT DOCUMENTS 896645 10/1953 Fed. Rep. of Germany.
941191 3/1956 Fed. Rep. of Germany.
966334 7/1957 Fed. Rep. of Germany.

OTHER PUBLICATIONS

Brauns, The Chemistry of Lignin, Academic Press, Inc. (1952), p. 279.
Sarkanen & Ludwig, Lignins Occurrence, Formation, Structure and Reactions, Wiley–Interscience, pp. 527–528.

*Primary Examiner*—John Kight, III
*Assistant Examiner*—Amelia B. Yarbrough
*Attorney, Agent, or Firm*—Schuyler, Banner, Birch, McKie & Beckett

[57] ABSTRACT

An oil-in-water anionic bituminous emulsion is disclosed wherein an anionic emulsifier is prepared by reacting lignosulfonate with a sulfonyl chloride or bromide of benzene or toluene or substituted benzene or an aliphatic hydrocarbon with four or more carbon atoms.

24 Claims, No Drawings

ANIONIC BITUMINOUS EMULSIONS

This invention pertains to an anionic bitumen or asphalt emulsion. More particularly it relates to the preparation of an anionic bituminous emulsion using a particular anionic emulsifying agent and the compositions thereof.

Bitumen or asphalt is widely used for many applications with paving and surface coatings possibly being the most extensive. While asphalt may be applied by different methods, there has been an increase in shift to emulsions, both cationic and anionic, to replace cutback or hot asphalt applications. Anionic emulsions are obtained by dispersing fine asphalt particles in a continuous water phase generally utilizing an anionic emulsifier to impart anionic characteristics to the emulsified asphalt particles.

The use of spent sulfite liquor or lignosulfonate as an anionic emulsifier as well as the use of ammonium lignosulfonate has been disclosed in U.S. Pat. Nos. 2,332,542 and 2,494,708. Calcium lignosulfonate, in U.S. Pat. No. 2,978,342, has been suggested as an anti-stripping agent for use in hot asphalt applications to enhance the coating and bonding of the hot asphalt to wet aggregate such that it will not readily be displaced or stripped from the aggregate upon being subjected to water. The reaction of alkali lignins with primary and secondary amines and formaldehyde in the Mannich-type reaction has been disclosed for preparation of anionic and cationic asphalt emulsifiers in U.S. Pat. Nos. 3,123,569 and 3,126,350. U.S. Pat. Nos. 3,718,639 and 4,017,419 disclose further reactions of lignosulfonate with amines and other constituents in preparation of asphalt emulsifiers. Anionic bituminous emulsions are disclosed in U.S. Pat. No. 4,088,505 where a mixture of alkali lignin with an adduct of ethylene oxide and an alkyl phenol are used as emulsifiers. While satisfactory results can be obtained by certain types of emulsifiers, efforts are continuously being made to develop more effective surfactants or emulsifiers to improve the performance of the emulsions.

It is, therefore, an object of this invention to provide an effective anionic bitumen emulsion. Another object is to provide an anionic asphalt emulsion employing a lignin-base anionic emulsifier. A further object is to provide a modified lignosulfonate that will emulsify asphalt without the co-addition of a synthetic surfactant. A still further object is to provide an anionic emulsion that meets ASTM specifications and has good aggregate coating properties.

The above and other objects are attained by this invention which comprises an oil-in-water anionic bituminous emulsion containing from 30 to 75 weight percent, preferably 55 to 65%, of the emulsion of bitumen dispersed in an aqueous continuous phase and from 0.1 to 5 weight percent of an anionic emulsifier prepared by reacting a lignosulfonate with a sulfonyl chloride or bromide of benzene, substituted benzene, toluene, or aliphatics with four or more carbon atoms until at least 30% of the phenolic hydroxyls of the lignosulfonate have reacted, and water in an amount to make up the balance. By reacting the lignosulfonate with the sulfonyl chloride or bromide, an anionic asphalt emulsifier is obtained which will give smooth, fine-particle asphalt emulsions that are stable towards settling and which show excellent to exceptionally good aggregate coating properties. The emulsions mix well with dense and/or clay containing aggregates to give uniformly dark consolidated structures having high strength.

The various methods known in the art for reaction of lignosulfonate with the sulfonyl halides may be used for preparation of the lignosulfonate-sulfonyl halide reaction product. In addition to carrying out the reaction under anhydrous conditions, the reaction may be simply carried out by adding the sulfonyl halide to an aqueous lignosulfonate solution to form a suspension or emulsion and mixing the reaction usually for from 12 to 60 hours until the desired extent of reaction has occurred. The sulfonyl halides are reactive and will react with the lignosulfonate at room temperature even though the reaction may be carried out at temperatures up to about 45° C., preferably at temperatures below about 35° C. At the higher temperatures the sulfonyl halide hydrolyzes at a much more rapid rate. Preferably the reaction is carried out under alkaline conditions or in the presence of an acid acceptor. Alkali and alkaline earth metal oxides or hydroxides may be used as acid acceptors to impart the alkaline condition or react with the halogen acid as it is liberated. Non-reactive amines may also be used for this purpose. The reaction may also be carried out in the presence of a sulfonyl halide solvent such as chloroform, dichloromethane, benzene, toluene and xylene. Since lignosulfonate is a surfactant, the lignosulfonate solution may be emulsified with the solution of the halide to effect the reaction. Somewhat improved results may be obtained by use of a halide solvent and also by employing of a small amount of a phase transfer agent such as, for example, ethyl triphenylphosphonium iodide, benzyltriphenylphosphonium chloride, or tetrabutylphosphonium acid acetate. The lignosulfonate solutions used may have a concentration of from about 10 to 40%. Higher concentrations may be employed but viscous reaction mixtures may be obtained making it more difficult to carry out. Likewise, more dilute solutions may be used, however the reaction proceeds at a slower rate and also more of the sulfonyl halide is lost through hydrolysis. The lignosulfonate must be reacted with sufficient amount of the sulfonyl halide such that at least about 30%, preferably from 45 to 65%, of the phenolic hydroxyls of the lignosulfonate have been reacted with the sulfonyl halide. For example, many lignosulfonates or spent sulfite liquors after fermentation may have a phenolic hydroxyl content of about 1.5% which must generally be reduced to a content of about 1% or less. The amount of sulfonyl halide necessary to be reacted with the lignosulfonate will vary depending upon the conditions employed. If the reaction is effected under anhydrous conditions substantially all of the sulfonyl chloride added would probably react with the phenolic hydroxyl. However, in carrying out the reaction in the presence of an aqueous solution, some of the sulfonyl halide is hydrolyzed even at room temperature and, thus, not utilized in the desired reaction. Generally in employing a stoichiometric amount of the sulfonyl halide in a solvent for reaction with lignosulfonate in an aqueous solution, the phenolic hydroxyl of the lignin can be reduced to about 50% of its original content and can be reduced to less than 30% of the original content by employing a modest excess of the sulfonyl halide. While the phenolic hydroxyls may be substantially all reacted, the effectiveness of the product does not greatly improve after the phenolic hydroxyl content of the lignosulfonate has been reduced to about 50% of its original content or for many products to a phenolic hydroxyl content of about 0.8 weight percent.

In the reaction, organic sulfonyl chlorides or bromides may be used. Such organic substituents include aliphatic hydrocarbons having at least four carbon atoms (e.g., butane and higher hydrocarbons having, for example, up to 10 carbon atoms or more), benzene, or benzene substituted with methyl, ethyl, chloro, bromo, carbomethoxy (i.e., $COOCH_3$) or nitro groups. The organic group chosen is one that increases the compatability of the lignosulfonate with the asphalt. Toluenesulfonyl chloride is preferred mainly because of its availability and more convenient handling.

The lignosulfonates used in reaction with the sulfonyl halides may be obtained by sulfonation of lignin obtained from any source by the various known methods. One of the main sources of lignosulfonate is the residual pulping liquors of the paper and pulp industries where lignocellulosic materials such as wood, straw, corn stalks, bagasse, and the like are processed to separate the cellulose or pulp from the lignin. In the sulfite pulping process, the lignocellulosic material is digested with a bisulfite or sulfite to obtain a sulfonated residual pulping liquor commonly referred to as "spent sulfite liquor" wherein the sulfonated lignin is dissolved. In other pulping processes, the residual pulping liquor as obtained from the process may not be a sulfonated product. However, the residual liquors or products containing the lignin portion of the lignocellulosic materials from the sulfite or other processes may be treated by the various known methods to sulfonate the lignin to the different degrees desired. For example, the residual liquor obtained in an alkaline process of digestion of lignocellulosic materials such as kraft, soda and other alkali processes may be sulfonated by reacting the product with a bisulfite or sulfite to obtain a sulfonated residual pulping liquor. Likewise, lignins known as "hydrolysis lignin" obtained from the hydrolysis of lignocellulosic materials in manufacturing wood sugars, or "hydrotropic lignins" derived from hydrotropic pulping processes may be sulfonated and used.

The sulfonated products obtained by sulfonation of lignin may be salts of certain cations, such as magnesium, calcium, ammonium, sodium, potassium, and the like. The lignosulfonates thus obtained may be used as such for the reaction or may be converted to lignosulfonic acid by addition of acid or use of ion exchange resins, and used or converted to salts or complexes of metals or cations other than those obtained in the sulfonation processes. The alkali metal salts are preferred. The products also usually contain many other constituents besides sulfonated lignin. For example, spent sulfite liquor generally contains about 40 to 60 weight percent of the lignosulfonate with the remainder being carbohydrates and other organic and inorganic compounds dissolved in the liquor. While the non-lignin constituents may be removed by various known methods, it is not necessary to do so. Some of the sulfonyl halide may be lost by reaction with certain non-lignin constituents but the amount is not excessive. Also, the sulfonated products, such as spent sulfite liquor, may be subjected to various pre-treatments, such as fermentation, oxidation or heat treatment under alkaline or acid conditions.

The anionic emulsifier of this invention is water soluble. In using the anionic emulsifier, the normal procedures used for the formation and application of bituminous emulsions may be followed. Generally, the reaction product of lignosulfonate with the sulfonyl halide, as an aqueous solution at around pH 11, is intimately contacted with a suitable bitumen in a mixing device, such as a colloid mill, which is capable of producing a vigorous shearing action. The bitumen content of the emulsion can range from 30 to 75 weight percent of the emulsion depending upon the intended use, preferably about 55 to 65% by weight. The anionic emulsifier is present in the final emulsion in a concentration ranging from about 0.1 to about 5% by weight of the emulsion, preferably from about 0.5 to about 2% by weight of the emulsion. While the aqueous solution of the emulsifier is generally used on the alkaline side, pHs from 3 to 12 may be used.

The bitumen used in the emulsion may be derived from Venezuela, mid-continent, western and other bitumen sources and also includes, in addition to bitumen, natural asphalt and the like. Practically any asphalt with penetration values ranging from 40 to about 300 may be emulsified with the aid of the emulsifier of this invention.

The following examples further illustrate the invention.

EXAMPLE I

A fermented calcium base spent sulfite liquor was converted to the sodium base by addition of sodium hydroxide and sulfuric acid and subjected to a mild alkaline treatment. The sodium base lignosulfonate or spent sulfite liquor had a phenolic hydroxyl content of 1.5%. To an aqueous solution of the lignosulfonate containing 25 weight percent of solids, sodium hydroxide solution and toluene were added followed by addition of benzenesulfonyl chloride and the reaction mixture reacted by mixing the mixture overnight and then allowed to set at room temperature three additional days.

On the basis of 100 grams of the dry sodium base spent sulfite liquor solids, 16.4 grams of benzenesulfonyl chloride were added which represented about the stoichiometric amount necessary to react with the phenolic hydroxyls of the lignosulfonate. On the same basis, toluene in an amount of 156 ml and 4 grams of sodium hydroxide were used. A phase transfer agent of ethyl triphenylphosphonium iodide in an amount of 1 gram was also used. It was added after the addition of the benzenesulfonyl chloride. After removal of toluene by vacuum evaporation of the reacted mixture, 123 grams of solids were recovered. The reaction product had a phenolic hydroxyl content of 0.58% based upon the original weight of the lignosulfonate sample or spent sulfite solids used in the reaction.

The phenolic hydroxyl content of lignosulfonate was determined by the UV difference method described by O. Goldschmid in Analytical Chemistry 26, 1421 (1954) and applying corrections for interference from conjugated carbonyl groups. In the procedure, the ultraviolet difference spectra of a pH 5 solution from that of a pH 12 solution at 300 and 350 nm are used to determine phenolic hydroxyl based on data obtained with model compounds. While results obtained on modified lignosulfonate may not be the absolute values, they are representative of the relative amounts of phenolic hydroxyl present. The presence of the hydrolysis product of organic sulfonyl compounds such as p-toluene sulfonic acid which contain no phenolic hydroxyl do not interfere with the phenolic hydroxyl determination.

The above product was tested as an anionic asphalt emulsifier.

EXAMPLE II

A fermented calcium base spent sulfite liquor was converted to the sodium salt and reacted with toluenesulfonyl chloride.

To a concentrated lignosulfonate solution containing 200 grams of dry solids, a 50% sodium hydroxide solution was added to adjust the pH of the sodium base lignosulfonate to a pH of 9. The mixture was then diluted to 500 ml with water to which 200 ml of toluene were added. While the mixture was being stired, 0.2 grams of ethyl triphenylphosphonium iodide was added after which the toluenesulfonyl chloride addition was made in an amount of 27 grams, which represented about 79% of the stoichiometric amount required for reaction with the phenolic hydroxyls. After addition of the toluenesulfonyl chloride, an additional 11.2 grams of 50% sodium hydroxide solution were added. The reaction mixture was stirred for three days at which time the pH dropped to 7.1. After stripping the toluene from the reaction mixture, 705 grams of solution were obtained. The lignosulfonate in the product had a phenolic hydroxyl content of 0.86% based on the original weight of the lignosulfonate sample or spent sulfite solids used in the reaction. The product was tested as an asphalt emulsifier.

EXAMPLE III

Toluenesulfonyl chloride in powder form was reacted with a lignosulfonate solution in a manner similar to that described in Example II except that no toluene was used and the pH of the reaction mixture was periodically checked and adjusted to about 11 by addition of sodium hydroxide solution having a concentration of about 10 weight percent. The reaction mixture was maintained at less than 25° C. Since p-toluenesulfonyl chloride is insoluble in water and melts at 69°–71° C., it modifies the lignosulfonates in this preparation by a solid/liquid reaction. The reaction mixture was stirred for three days at which time the pH had dropped to 8.7 and was adjusted to 11 by addition of the caustic solution. A total of about 170 grams of the sodium hydroxide solution was added which represented about 17 grams of sodium hydroxide. The mixture was allowed to set for two additional days at which time the pH had dropped to 10.6. The solution was concentrated to 558 grams by vacuum evaporation. No insolubles were found in the product solution. The lignosulfonate in the product had a phenolic hydroxyl content of 0.76% based on the original weight of the lignosulfonate sample or spent sulfite solids used in the reaction. The product was tested as an anionic asphalt emulsifier.

EXAMPLE IV

The spent sulfite liquor, similar to that described in Example III, was reacted with toluenesulfonyl chloride in a manner similar to that described above except that the amount of the sulfonyl chloride used was increased to 40 grams which was equivalent to about 1.2 times the stoichiometric amount necessary to react with the phenolic hydroxyl.

The mixture was stirred for about three days and then allowed to set for an additional nine days at which time the pH was periodically adjusted to about 11. Upon concentrating the solution, the product obtained contained 0.45 weight percent of phenolic hydroxyl based on the original weight of the lignosulfonate sample or spent sulfite solids used in the reaction. It was also tested as an anionic asphalt emulsifier.

EXAMPLE V

The spent sulfite liquor similar to that described in Example II was reacted with toluenesulfonyl chloride in a manner similar to that described in Example III except that no phase transfer agent was added. Also, the reaction mixture was mixed for two days after which the solution was concentrated to about 550 grams by vacuum evaporation. The product obtained contained 0.96% of phenolic hydroxyl based on the original weight of the lignosulfonate sample or spent sulfite solids used in the reaction.

A second run was also made in a manner similar to that described above except that ethyl triphenylphosphonium iodide as a transfer agent was added in an amount of 1 gram which represented about 0.5 weight percent on a dry solids basis of the sodium base spent sulfite liquor or lignosulfonate reacted. After reaction for two days, the solution was evaporated under vacuum to 547 grams. The product has a phenolic hydroxyl content of 0.90% based on the original weight of the lignosulfonate sample or spent sulfite solids used in the reaction, and was tested as an anionic asphalt emulsifier.

EXAMPLE VI

The spent sulfite liquor similar to that described in Example II was reacted with 4-chlorobenzenesulfonyl chloride in powder form in an amount of 30 grams in a manner similar to that described in Example III except that no phase transfer reagent was added and except that the pH of the reaction mixture was periodically checked and adjusted to about 10 by addition of sodium hydroxide solution having a concentration of about 20 weight percent. The reaction mixture was stirred for five days at which time the pH had dropped to 9.6 and was adjusted to 11 by addition of the caustic solution. A total of 112 grams of the sodium hydroxide solution was added which represented about 22 grams of sodium hydroxide. The solution was concentrated to 538 grams by vacuum evaporation. The lignosulfonate in the product had a phenolic hydroxyl content of 0.84% based on the original weight of the lignosulfonate sample or spent sulfite solids used in the reaction. The product was tested as an anionic asphalt emulsifier.

The spent sulfite liquor similar to that described in Example II had its pH adjusted to about 11 by the addition of sodium hydroxide solution having a concentration of about 50 weight percent. The product was tested as an anionic asphalt emulsifier as a control.

EXAMPLE VII

The spent sulfite liquor similar to that described in Example II was reacted with methanesulfonyl chloride in an amount of 30 grams in a manner similar to that described in Example III except no phase transfer reagent was added. The pH of the reaction mixture was periodically checked and adjusted to about 11 by addition of sodium hydroxide solution having a concentration of about 20 weight percent. The reaction mixture was stirred for four days at which time the pH had dropped to 10.8 and was adjusted to 11 by addition of the caustic solution. A total of 134 grams of the sodium hydroxide solution was added which represented about 27 grams of sodium hydroxide. The solution was concentrated to 476 grams by vacuum evaporation. The lignosulfonate in the product had a phenolic hydroxyl content of 0.81% based on the original weight of the lignosulfonate sample or spent sulfite solids used in the reaction. The product was tested as an anionic asphalt emulsifier.

EXAMPLE VIII

The spent sulfite liquor similar to that described in Example II was reacted with butanesulfonyl chloride in an amount of 56 grams in a manner similar to that described in Example III except that no phase transfer reagent was added and except that the pH of the reaction mixture was periodically checked and adjusted to about 10 by addition of sodium hydroxide solution having a concentration of about 20 weight percent. The reaction mixture was stirred for four days at which time the pH had dropped to 9.0 and was adjusted to 11 by addition of the caustic solution. A total of about 142 grams of the sodium hydroxide solution was added which represented about 28 grams of sodium hydroxide. The solution was concentrated to 641 grams by vacuum evaporation. The lignosulfonate in the product had a phenolic hydroxyl content of 0.25% based on the original weight of the lignosulfonate sample or spent sulfite solids used in the reaction. The product was tested as an anionic asphalt emulsifier.

EXAMPLE IX

A fermented calcium base spent sulfite liquor was converted to the sodium salt and reacted with carbomethoxybenzenesulfonyl chloride.

A concentrated lignosulfonate solution containing 300 grams of dry solids was diluted to 700 grams with water and the pH of the solution was adjusted to about 10 by addition of sodium hydroxide solution having a concentration of about 20 weight percent. The lignosulfonate solution was reacted with carbomethoxybenzenesulfonyl chloride in an amount of 60 grams. The pH of the reaction mixture was periodically checked and adjusted to about 10 by addition of the caustic solution. The reaction mixture was stirred for three days at which time the pH had dropped to 9.8 and was adjusted to 11 by addition of the caustic solution. A total of 175 grams of the sodium hydroxide solution was added which represented about 35 grams of sodium hydroxide. The solution was concentrated to 770 grams by vacuum evaporation. The lignosulfonate in the product had a phenolic hydroxyl content of 0.84% based on the original weight of the lignosulfonate sample or spent sulfite solids used in the reaction. The product was tested as an anionic asphalt emulsifier.

The products prepared in the Examples above were tested as anionic asphalt emulsifiers using procedures similar to those prescribed by ASTM for cement mixing test, 5-day settlement stability and sieve analysis.

The emulsions were prepared by heating the asphalt to a temperature of 133° C. and passing the asphalt and water heated to about 50° containing the emulsifier through a colloid mill. The asphalt used was an asphalt having a penetration of 120–150 with products of Examples I, VIII and IX, and an asphalt of 60–80 pen with products of Examples II to VII.

In addition to the above tests, the emulsion was evaluated by visual inspection of coatings obtained with a limited amount of emulsion on a sand-clay mixture by observing the color and uniformity of coating. The products were rated on a scale based on color where a score of 100 was assigned to an emulsion which coated the sand-clay mixture uniformly so that a dark brown color was obtained. This type of coating results in good strength. A score of 100 represents excellent coating whereas scores above 100 indicate exceptionally good coatings and scores below 80 were considered to indicate sub-standard coating properties.

The results are shown in the Table below.

| Run | Emulsifier | Emulsifier Use Level, %(a) | Emulsion Non-Volatiles %(a) | Emulsion Viscosity, Saybolt-Furol Seconds | Sieve Test, % Residue | 5-day Settlement, %(b) | Cement Mixing | Coating Score |
|---|---|---|---|---|---|---|---|---|
| 1 | Example I | 1.19 | 60.3 | 17 | 0 | 0.2 | Pass | 100 |
| 2 | Example II | 1.15 | 61.7 | 23 | 0 | 1.5 | Pass | 112 |
| 3 | Example III | 1.17 | 61.1 | 23 | 0 | 2.6 | Pass | 100 |
| 4 | Example IV | 1.16 | 61.3 | 26 | 0 | 1.8 | Pass | 112 |
| 5 | Example V without phase transfer agent | 1.14 | 62.0 | 27 | 0 | 3.3 | Pass | 100 |
| 6 | Example V with phase transfer agent | 1.12 | 62.5 | 33 | 0 | 1.7 | Pass | 100 |
| 7 | Example VI | 1.15 | 61.7 | 21 | 0 | 2.1 | Pass | 112 |
| 8 | Example VI Control | (1.2) | | No emulsion formed | | | | |
| 9 | Example VII | (1.2) | | No emulsion formed | | | | |
| 10 | Example VIII | 1.12 | 62.8 | 20 | ~0.2 | 1.8 | Pass | 112 |
| 11 | Example IX | 1.14 | 61.9 | 15 | ~0.2 | 4.1 | Pass | 112 |

(a)Versus the final emulsion
(b)Maximum permissible settlement is 5%.

I claim:

1. An oil-in-water anionic bituminous emulsion which comprises from about 30 to about 75 weight percent of the emulsion of bitumen dispersed in an aqueous continuous phase, and from 0.1 to 5 weight percent of an anionic emulsifier prepared by reacting a lignosulfonate with an organic sulfonyl chloride or bromide in which the organic group is selected from the group consisting of benzene, substituted benzene, and an aliphatic hydrocarbon having at least four carbon atoms until at least 30% of the phenolic hydroxyls on the lignosulfonates have been reacted.

2. A composition according to claim 1 wherein the lignosulfonate is reacted with toluenesulfonyl chloride.

3. A composition according to claim 1 wherein the lignosulfonate is reacted with benzenesulfonyl chloride.

4. A composition according to claim 1 wherein the lignosulfonate is reacted with 4-chlorobenzenesulfonyl chloride.

5. A composition according to claim 1 wherein the lignosulfonate is reacted with butanesulfonyl chloride.

6. A composition according to claim 1 wherein the lignosulfonate is reacted with carbomethoxybenzenesulfonyl chloride.

7. A composition according to claim 1 wherein the lignosulfonate is reacted with said sulfonyl chloride or bromide until from 40 to 70% of the phenolic hydroxyls on the lignosulfonates have been reacted.

8. A composition according to claim 7 wherein the lignosulfonate is reacted with toluenesulfonyl chloride.

9. A composition according to claim 7 wherein the lignosulfonate is reacted with benzenesulfonyl chloride.

10. A composition according to claim 7 wherein the lignosulfonate is reacted with 4-chlorobenzenesulfonyl chloride.

11. A composition according to claim 7 wherein the lignosulfonate is reacted with butanesulfonyl chloride.

12. A composition according to claim 7 wherein the lignosulfonate is reacted with carbomethoxybenzenesulfonyl chloride.

13. A composition according to claim 7 wherein the emulsion contains from 55 to 65 weight percent of bitumen and from 0.5 to 2 weight percent of the anionic emulsifier.

14. A composition according to claim 13 wherein said anionic emulsifier is prepared by reacting lignosulfonate with toluenesulfonyl chloride.

15. A composition according to claim 13 wherein said anionic emulsifier is prepared by reacting lignosulfonate with benzenesulfonyl chloride.

16. A composition according to claim 13 wherein said anionic emulsifier is prepared by reacting lignosulfonate with 4-chlorobenzenesulfonyl chloride.

17. A composition according to claim 13 wherein said anionic emulsifier is prepared by reacting lignosulfonate with butanesulfonyl chloride.

18. A composition according to claim 13 wherein said anionic emulsifier is prepared by reacting lignosulfonate with carbomethoxybenzenesulfonyl chloride.

19. A composition according to claim 1 wherein the lignosulfonate is reacted with said sulfonyl chloride or bromide until the phenolic hydroxyl content of the lignosulfonate is in the range of 1.0 to 0.45 weight percent based on the original lignosulfonate sample or spent sulfite liquor solids used in the reaction.

20. A composition according to claim 19 wherein the lignosulfonate is reacted with toluenesulfonyl chloride.

21. A composition according to claim 19 wherein the lignosulfonate is reacted with benzenesulfonyl chloride.

22. A composition according to claim 19 wherein the lignosulfonate is reacted with 4-chlorobenzenesulfonyl chloride.

23. A composition according to claim 19 wherein the lignosulfonate is reacted with butanesulfonyl chloride.

24. A composition according to claim 19 wherein the lignosulfonate is reacted with carbomethoxybenzenesulfonyl chloride.

* * * * *